United States Patent [19]

Scheindlin

[11] 4,341,783

[45] Jul. 27, 1982

[54] TOPICAL USE OF DYPHYLLINE AND DYPHYLLINE CONTAINING COMPOSITIONS

[75] Inventor: Stanley Scheindlin, 3011 Nesper St., Philadelphia, Pa. 19152

[73] Assignee: Lemmon Company, Sellersville, Pa.

[21] Appl. No.: 174,090

[22] Filed: Jul. 31, 1980

[51] Int. Cl.$^3$ ............................................. A61K 31/52
[52] U.S. Cl. ..................................................... 424/253
[58] Field of Search ......................................... 424/253

[56] References Cited

U.S. PATENT DOCUMENTS 2,575,344  11/1951  Jones et al. ........................... 544/267
4,061,753  12/1977  Bodor et al. ......................... 424/253
4,141,976  2/1979   Voorhees ............................. 424/240

OTHER PUBLICATIONS

Chemical Abstracts, 91: 89040n, (1979).

Primary Examiner—Leonard Schenkman
Attorney, Agent, or Firm—Caesar, Rivise, Bernstein & Cohen, Ltd.

[57] ABSTRACT

Dyphylline is used preferably as the active ingredient in a cream base for topical application to the skin in the treatment of psoriasis and atopic dermatitis. The invention involves the method of use of dyphylline, as well as dyphylline containing compositions.

4 Claims, No Drawings

TOPICAL USE OF DYPHYLLINE AND DYPHYLLINE CONTAINING COMPOSITIONS

This invention relates to the treatment of psoriasis and other diseases of the skin by the topical administration of dyphylline, preferably in the form of a cream-based composition.

Current therapy of psoriasis depends on the extent and severity of the initial involvement and the age of the patient at the onset. Complete and permanent remission rarely occurs. Early lesions are more amenable to treatment than long-standing ones. Acute attacks usually clear up, but recurrence is almost certain. No therapeutic method assures a cure. Prolonged use usually reduces the effectiveness of any agent. Supportive treatment should include adequate rest and diet, attention to intercurrent illnesses, elimination of possible infectious foci, and psychotherapy if needed. Exposure to natural sunlight in moderate doses is recommended, although in occasional instances, it may induce exacerbations.

The simplest forms of treatment are advisable initially. Because of the limited number of effective remedies, it is unwise to shift too rapidly from one treatment to another. Daily removal of scales with soap and water and a soft brush, followed by application of a keratolytic ointment, may be tried. New topical adrenocortical steroid preparations have largely superseded many previous local treatments for psoriasis. These include fluocinolone (0.01 to 0.025%), flurandrenolone (0.025%) and triamcinolone acetonide (0.05%) creams. These are most effective if covered with a polyethylene film after application at bedtime. In small localized lesions, an intralesional injection of 1% triamcinolone acetonide suspension often produces involution for many weeks. Alternate treatments include (for the scalp) a tar-sulfur-salicylic acid combination; anthralin ointment, 0.1 to 1.0% applied once a day to lesions on the body; various forms of tar, such as colorless tar distillate preparations; and 5% crude coal tar in Lassar's paste.

An effective method of treatment, usually given in hospitals, is the Goeckerman regimen: every night crude coal tar ointment, 5%, is rubbed thoroughly into all affected areas (except the scalp); in the morning the tar is removed with mineral oil. Then the involved parts are exposed daily to ultraviolet radiation or natural sunlight. The duration of exposure is increased progressively just to the point of mild erythema. In many cases, involution of most of the lesions may occur in 10 to 14 days. This method of treatment is based on the photosensitizing effect of the coal tar.

Systemic ardrenocortical steroid therapy has been effective in about 50% of patients treated. It should be used only in severe intractable disease, because treatment often must be prolonged and discontinuance without flare-up at times may be impossible. The newer steroids are preferred.

X-ray therapy can be used for psoriasis of the nails and also for large, thick, resistant plaques on the legs. This therapy is used much less frequently than previously because of potential dangers.

The treatment of psoriasis with psoralen (methoxsalen) and direct sunlight has been reported as successful but unpredictable because of its dependence on prevailing weather conditions which are subject to marked daily and seasonal variations. A study carried out in a locale nearly ideal because of is reliable year-round sunshine (Tucson, Arizona) produced complete remission of all exposed plaques in twelve consecutive patients (Basler, Rodney, S. W. M.D.: Psoralen and sunlight for psoriasis in the southwest, Cutis 24: 386–388, 1979).

The PUVA regimen, which is similar, consists of using oral psoralen and long wave UV light bulbs (320–400 nm.).

The psoralen is activated by the sunlight or UV light and inhibits DNA synethesis in epithelial cells. Normal cells grow and this controls the psoriasis.

Methotrexate inhibits folic acid which results in the same effect. Methotrexate is only indicated for the very severe psoriasis. It is used orally either in a weekly single dose, divided daily dose or a weekly dose divided into 3 or 4 doses 8 to 12 hours apart. Once optimal clinical response is achieved, dosage is reduced to the lowest amount possible with the longest rest period between doses. Methotrexate may permit return to conventional topical therapy which should be encouraged.

It has been further proposed in an article entitled "Trials with Xanthine Derivatives in Systemic Treatment of Psoriasis" by Iancu, Schneur and Cohen (Dermatologica, 159; 55–61 (1979)) to use both dyphylline and aminophylline in oral administration for the treatment of psoriasis. The xanthine derivatives administered orally had a limited effect and not every psoriatic patient responded to the treatment. Patients with widespread and active psoriatic lesions, with a tendency to develop erythrodermia or pustular lesions, reacted with a high degree of skin dryness which produce a very uncomfortable feeling. A patient with a history of erythrodermia and recurring widespread psoriatic lesions reacted to dyphylline treatment with dryness of almost all of the skin surface, edema of the lower limbs, particularly legs and feet, and with high temperature. These side effects subsided in about ten days, after discontinuation of treatment and without antibiotics. The patient was then treated with methotrexate.

The aforesaid treatment was also without effect in two cases of psorias geographica which covered a large skin area. Since the psoriatic lesions are a proliferative reaction to the cyclic AMP/cyclic GMP imbalance, the authors concluded that psoriasis might be considered a benign, superficial, proliferative, skin-tumor like condition, and concluded that a relationship exists between xanthine dose and tumor load. However, the authors conceded that while the foregoing assumption might explain the failure of the oral administration of xanthine derivatives in widespread and psoriasis geographica cases, the foregoing assumption could not explain the failure in a patient with relatively limited lesions in the arms and left thigh.

The authors then concluded that other factors, such as degree of absorption or interference with the inhibitory effect of xanthine derivatives against phosphodiesterase at the cellular level of the psoriatic lesion might exist.

In conclusion, the authors noted that dyphylline was administered in high dosages and no significant side-effects were observed. The liver function of the patients was normal during treatment, and only occasionally patients complained of dizziness, nausea and headache. Accordingly, the authors believed that the elucidation and neutralization of possible interfering factors might lead to a very comfortable treatment for most psoriatic patients.

In another article entitled "Monocyte Function in Psoriasis" by Bar-Eli, Gallily, Cohen and Wahba (1979), the authors reported recent treatment of psoriatic patients with orally administered dyphylline as yielding encouraging results. The authors reported that the rationale for the oral administration of dyphylline was that dyphylline might increase the intracellular levels of cyclic AMP, thus restoring the presumably decreased intraepidermal cAMP/cGMP ratio in the lesional epidermis of psoriasis to normal. The conclusion reached was stated by the authors as supporting the hypothesis that psoriatic abnormality is not confined to only one type of cell, the epidermal cell, as was previously assumed.

In accordance with the present invention, a topical use of dyphylline is proposed, with the dyphylline being present in a cream-based composition, rather than being orally administered.

When administered orally, dyphylline has certain disadvantages. First, a relatively high milligram-dosage is required to attain effective levels of the drug in the blood. Second, dyphylline is rapidly excreted and has a half-life of about 2.2 hours, requiring frequent dosing.

However, dyphylline has certain properties which make it uniquely suitable for application directly to the desired site of action. These properties are: its high water-solubility, and its neutral pH. Thus, it is possible to administer dyphylline by inhalation as set forth in pending Application Ser. No. 113,847, filed Jan. 21, 1980, the entire disclosure of which is incorporated herein by reference. By the foregoing, it relieves bronchoconstriction while the dyphylline blood level is well below that needed for systemic effectiveness. Dyphylline's high solubility enables a high concentration to be delivered directly into the lungs, and by virtue of its neutral pH it is non-irritating to the bronchial tissues.

Another body tissue which may be directly treated is the skin. The cells of the skin contain cyclic adenosine monophosphate (cAMP) and cyclic guanosine monophosphate (cGMP) as well as the phosphodiesterase enzyme which destroys these substances. Certain skin diseases are characterized by disturbances in the absolute concentrations of cAMP and cGMP, or in the ratio in which they are present. For example, in psoriasis the epidermal cells show increased levels of cGMP and decreased levels of cAMP. It has been found that high levels of cAMP enhance cell differentiation, while high levels of cGMP and low levels of cAMP enhance cell proliferation at the expense of differentiation. This is the metabolic abnormality in psoriasis.

The allergic condition known as atopic dermatitis is also associated with derangement of the skin cAMP and cGMP levels. Atopic dermatitis can be considered similar to an asthmatic condition localized in the skin. Hence, it is proposed to use phosphodiesterase inhibitors to normalize the skin cAMP and cGMP, and thus treat the atopic condition. Xanthine derivatives have been shown to be epidermal phosphodiesterase inhibitors.

Of the available Xanthine drugs, dyphylline is uniquely suitable for topical application. Its high solubility permits the formulation of dosage forms with a high concentration of available active ingredient, and its neutral pH renders it non-irritating. Also, in a suitably formulated topical dosage form, dyphylline remains in direct contact with the skin for a prolonged time, thus obviating the disadvantage of its short half-life.

Accordingly, dyphylline creams have been formulated. Preliminary clinical study has shown that a 10% dyphylline cream worked as well as 0.1% triamcinolone in patients with severe atopic dermatitis.

A preferred dyphylline cream in accordance with the present invention has the following composition:

Dyphylline: 10.0%
Stearic Acid: 15.0%
Cetyl Alcohol: 5.0%
Petrolatum, White: 3.0%
Polyoxyl 40 Stearate: 9.0%
Sorbitol Solution: 7.5%
Propylene Glycol: 7.5%
Methylparaben: 0.025%
Propylparaben: 0.015%
Purified Water q.s.: 100.0%

In order to prepare dyphylline cream in accordance with the aforesaid formulation, there is a first step of melting together the stearic acid, cetyl alcohol, white petrolatum, polyoxyl 40 stearate, methylparaben and propylparaben, to about 65° C. In a separate container, the sorbitol solution and propylene glycol are mixed and heated to about 67° C. The sorbitol-propylene glycol mixture is then added to the first mentioned six components which were melted together to about 65° C. Hot purified water in an amount of approximately 25% by weight to the combined weight of the aforesid eight components is added. The overall emulsion is mixed as the temperature is allowed to fall to about 50° C.

In a separate container, the dyphylline is mixed with about 20% by weight purified water. The dyphylline solution is added to the aforesaid emulsion slowly with continuously stirring. Mixing is continued as the temperature of the overall mixture is lowered to room temperature. Purified water is added to make up to 100% of desired weight, followed by mixing.

In the aforesaid formulation for dyphylline cream, numerous variations may be made without departing from the invention. The concentration of dyphylline can be varied between 0.5 to 25% by weight. The oil phase ingredients, stearic acid, cetyl alcohol and white petrolatum can be varied to adjust the consistency of the cream. The quantities of the humectants, sorbitol solution and propylene glycol may be varied. Both of these ingredients may be replaced in whole or in part by glycerol. The amounts of the preservatives, methylparaben and propylparaben, may be varied or replaced by other types of preservatives, e.g. sorbic acid and/or potassium sorbate, or thimerosal. The amount of the emulsifier, polyoxyl 40 stearate may be varied. It may be replaced by other emulsifiers, such as, sorbitan esters and polyoxyl derivatives thereof; triethanolamine and triethanolamine salts of fatty acids; glyceryl monostearate and diglycol stearate.

The aforesaid dyphylline cream formulation is an oil-in-water type cream or emulsion. Other types of topical vehicles which are also satisfactory are as follows:

(1) Oil in water emulsion lotions
(2) Water in oil emulsion creams
(3) Water in oil emulsion lotions
(4) Jelly (such as aqueous bases gelled with pectin, CMC, carbomer or other known thickeners)
(5) Polyethylene glycol based ointments (water soluble)

(6) Ointments comprised of, for instance, petrolatum, gelled mineral oil, lanolin, lanolin derivatives, hydrophilic petrolatum and similar agents.

From the foregoing, it can be seen that the present discovery involves the topical use of dyphylline for psoriasis treamtment, with the dyphylline being carried by a vehicle of sufficient viscosity to maintain the dyphylline in contact with the lesions. The dyphylline containing compositions of this invention used in the treatment of psoriasis, contain an effective amount of dyphylline. By virtue of the use of the dyphylline cream of the present invention, the dyphylline is placed in direct contact with the lesion and kept in direct contact for a substantial time. A preferred dosage is to apply the cream to the lesions a minimum of three times a day, or even four times a day, by rubbing the dyphylline cream into the lesions and leaving a thin coating on the surface of at least 0.2 mm thickness.

With the specific dyphylline cream formulation of this invention, there is provided a cream of better spreadability which achieves a softer film with excellent clinging properties. While the water component of the cream can be varied, a preferred amount of water is 44% by weight.

From the foregoing, it can be seen that there is provided treatment of psoriasis involving the direct application of dyphylline preferably in cream formulation to the lesions, thereby avoiding the larger dosage requirements and side effects of oral administration.

The creams of the present invention are also quite suitable in the treatment of atopic dermatitis.

Without further elaboration, the foregoing will so fully illustrate my invention that others may, by applying current or future knowledge, readily adapt the same for use under various conditions of service.

What is claimed as the invention is:

1. A method of treating psoriasis comprising applying directly to the psoriasis lesions an effective amount of dyphylline.

2. A method of treating atopic dermatitis comprising applying directly to the affected portions of the skin an effective amount of dyphylline.

3. A dyphylline containing composition for topical treatment of psoriasis or atopic dermatitis, comprising a cream base including an effective amount of dyphylline.

4. The composition of claim 3, which comprises the following:

Dyphylline: 10.0%
Stearic Acid: 15.0%
Cetyl Alcohol: 5.0%
Petrolatum, White: 3.0%
Polyoxyl 40 Stearate: 9.0%
Sorbitol Solution: 7.5%
Propylene Glycol: 7.5%
Methylparaben: 0.025%
Propylparaben: 0.015%
Purified Water q.s.: 100.0%

* * * * *